United States Patent [19]
Linden et al.

[11] Patent Number: 5,538,504
[45] Date of Patent: Jul. 23, 1996

[54] INTRA-EXTRAVASCULAR DRUG DELIVERY CATHETER AND METHOD

[75] Inventors: Bradley C. Linden, Minneapolis; Donald F. Palme, II, Dayton; Peter T. Keith, Fridley; Robert E. Atkinson, New Brighton, all of Minn.

[73] Assignee: SciMed Life Systems, Inc., Maple Grove, Minn.

[21] Appl. No.: 269,936

[22] Filed: Jul. 1, 1994

Related U.S. Application Data

[63] Continuation of Ser. No. 913,227, Jul. 14, 1992, abandoned.

[51] Int. Cl.$^6$ ............................................. A61M 31/00
[52] U.S. Cl. ........................... 604/53; 604/164; 604/264
[58] Field of Search .................................. 604/22, 46, 53, 604/96, 280, 164, 264, 272–274; 606/159, 167, 171, 194

[56] References Cited

U.S. PATENT DOCUMENTS 4,578,061  3/1986  Lemelson .
5,236,424  8/1993  Imran .

FOREIGN PATENT DOCUMENTS

WO92/10142  6/1992  WIPO .

*Primary Examiner*—Corrine M. McDermott
*Attorney, Agent, or Firm*—Brinks Hofer Gilson & Lione

[57] ABSTRACT

A drug delivery catheter is provided which includes a catheter comprised of an elongated tubular shaft with an inner lumen and a vessel puncturing element which is housed in the lumen. The puncturing element has a retracted position such that it will not be in contact with the vessel wall as the catheter is guided through the vasculature. The puncturing element also has a puncturing position where it protrudes radially outward of the catheter shaft and engages and punctures the vessel wall. The catheter is first inserted into the vessel to be treated and the puncturing element is positioned at the site in the vessel to be treated. The puncturing element is then moved to its puncturing position and the inner surface of the vessel wall is punctured. A drug is then delivered through the puncture. The drug may be delivered into either the vessel wall itself or to the outside of the vessel wall.

56 Claims, 5 Drawing Sheets

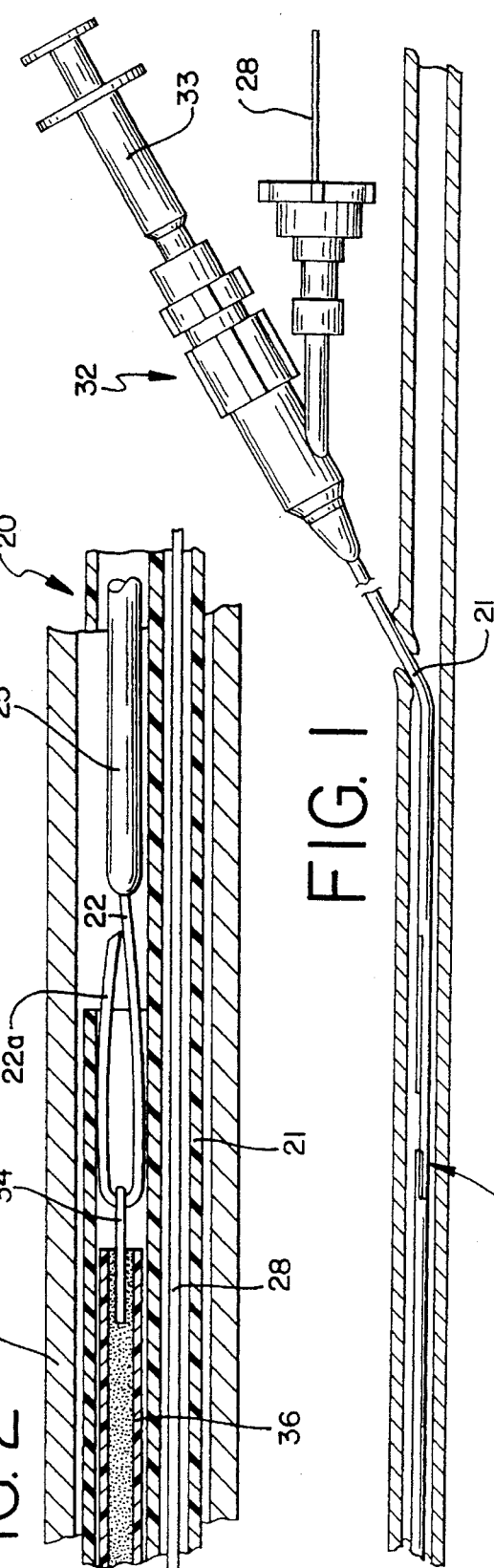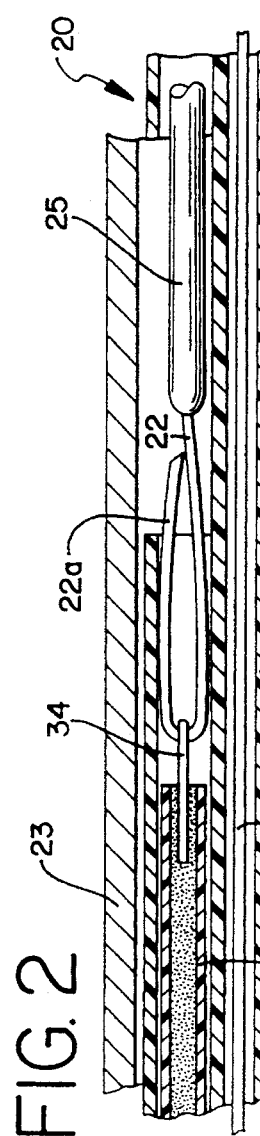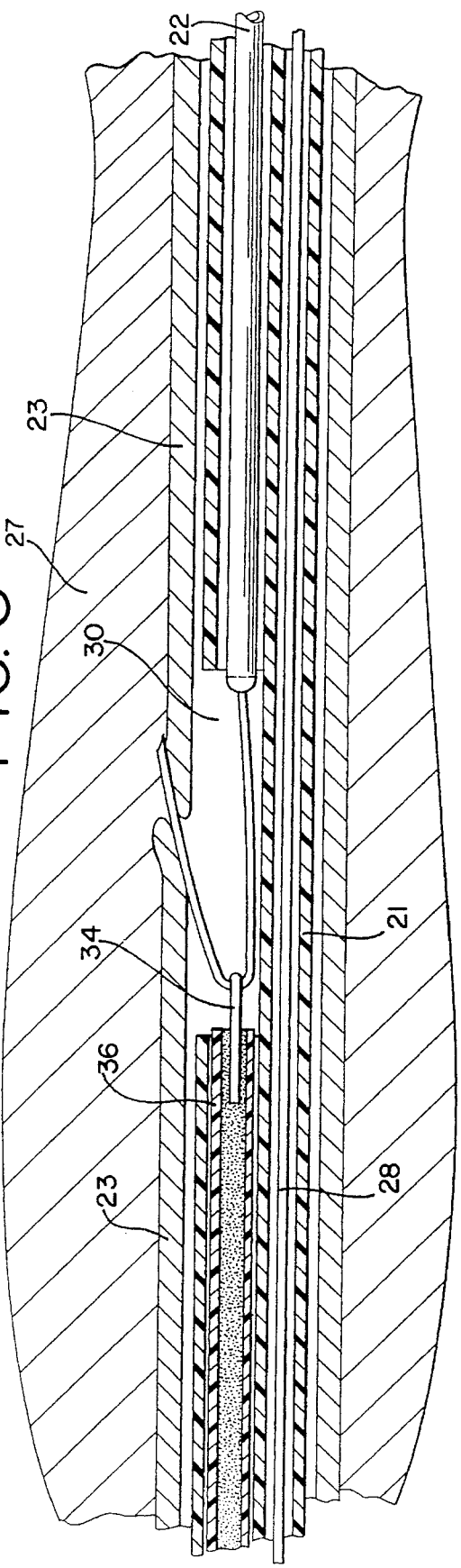

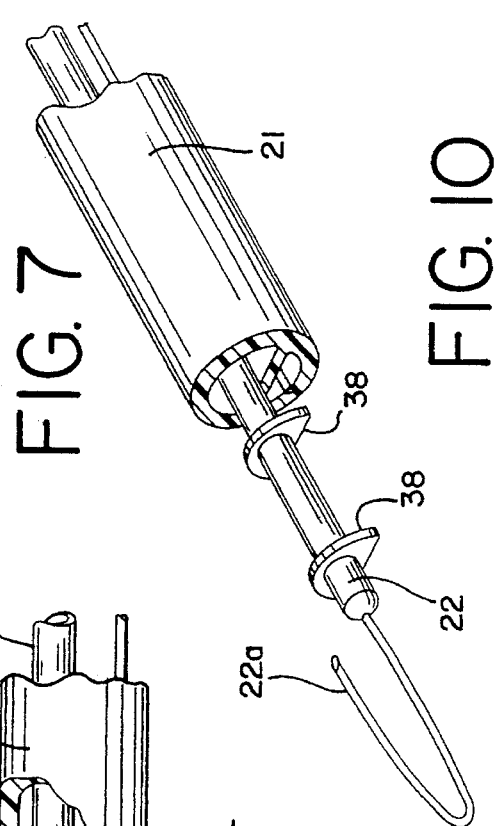
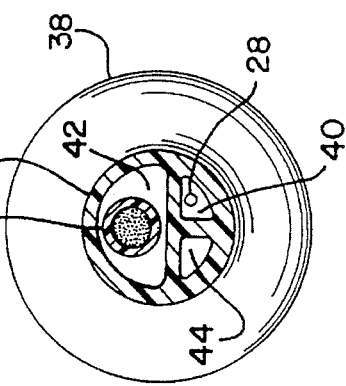
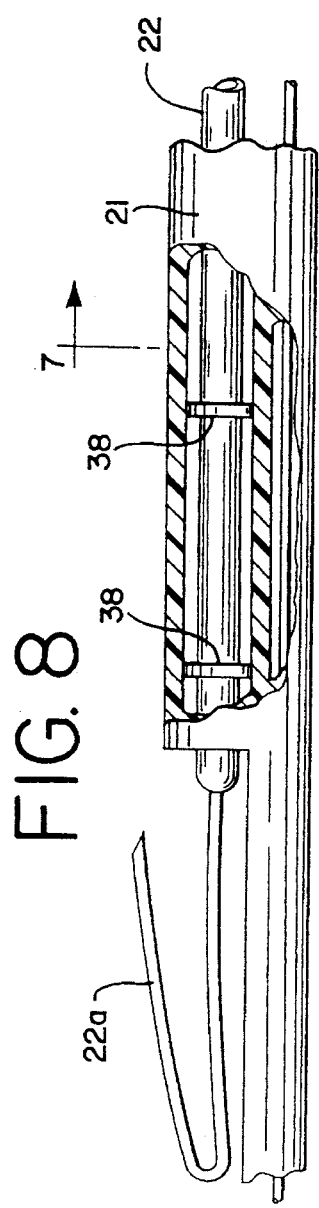
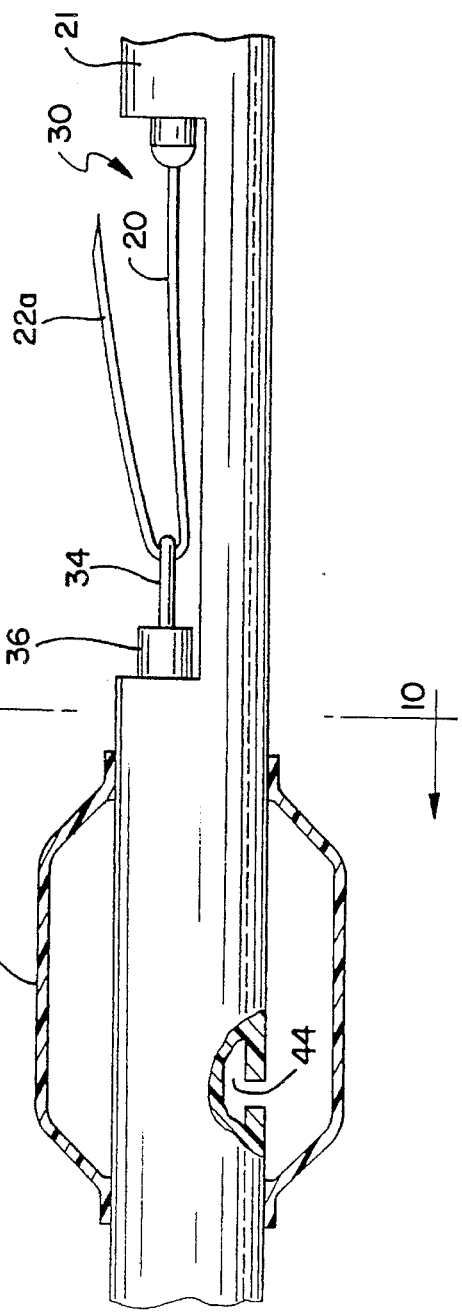

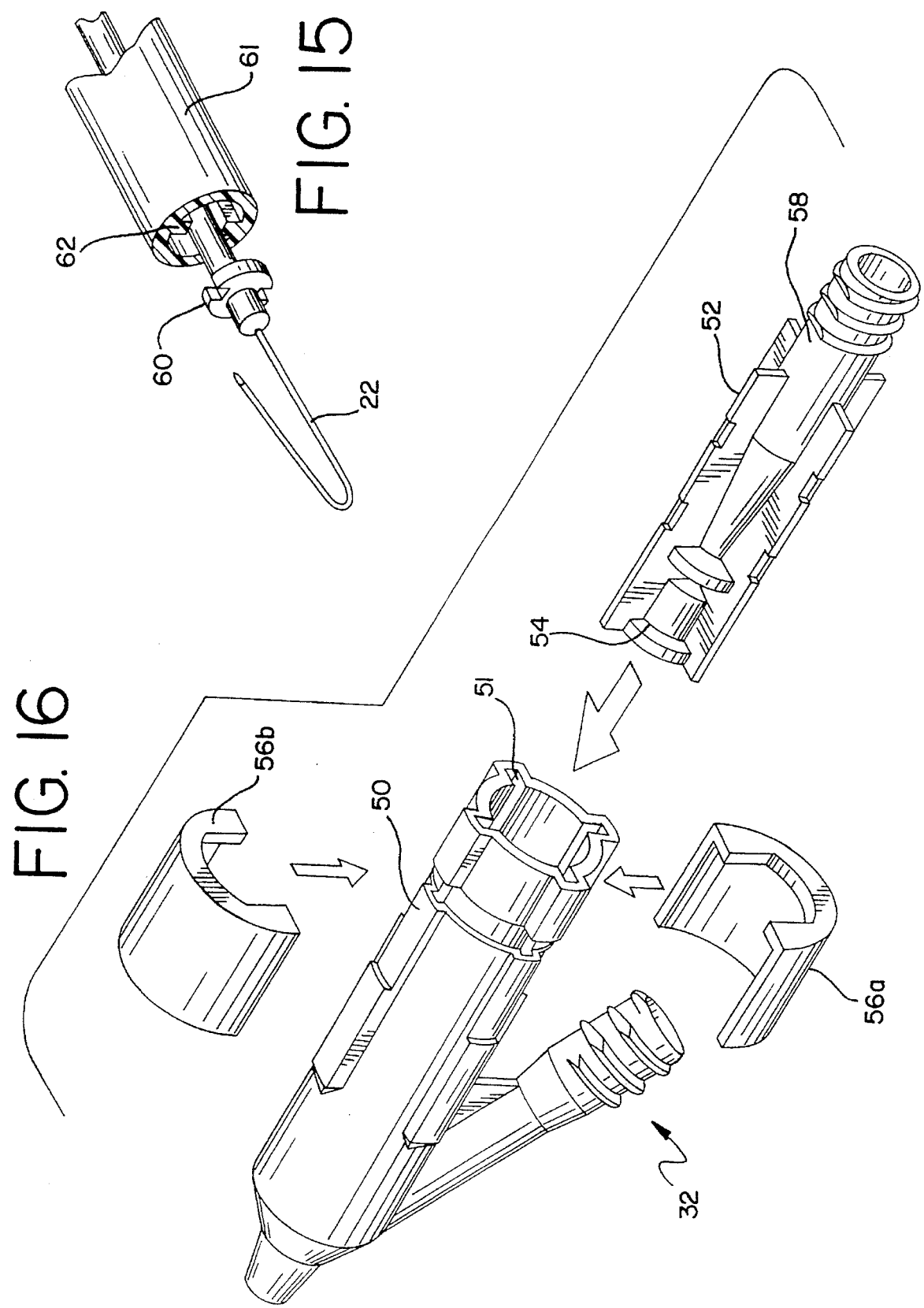

INTRA-EXTRAVASCULAR DRUG DELIVERY CATHETER AND METHOD

STATEMENT OF RELATED APPLICATIONS

This application is a continuation of U.S. patent application Ser. No. 07/913,227, filed Jul. 14, 1992, now abandoned, entitled "Intra-extravascular Drug Delivery Catheter and Method," and assigned to the assignees of the present invention.

BACKGROUND OF THE INVENTION

The present invention relates to a drug delivery device and method for delivering a drug agent to a vessel or vessel-like lumen in the body. More particularly, the present invention relates to a drug delivery device and method wherein the drug agent is delivered to the vessel wall or to the outside of the vessel wall.

Obstructive atherosclerotic disease is a serious health problem facing our society today. This disease is the result of the deposit of fatty substances and cells and connective tissue on the interior of the walls of the arteries. The build-up or accumulation of such deposits results in a narrowing of the inside diameter of the artery which in turn restricts the blood flow through the artery. This disease, wherein the opening or lumen of the artery is narrowed, is known as atherosclerosis and the accumulation is known as a lesion.

One commonly used procedure for treating an obstruction caused by atherosclerosis is a procedure known as coronary artery bypass graft surgery ("bypass surgery"). Although bypass surgery has been used with moderate success in the treatment of atherosclerosis, it is invasive and traumatic to the patient.

One less invasive and traumatic procedure developed more recently is coronary angioplasty. Coronary angioplasty, and angioplasty in general, is a procedure in which a balloon is positioned in the inside of the artery at the site of the accumulation or lesion and inflated in order to dilate the atherosclerotic lesion and thus open the restricted area of the artery. In order to advance the balloon to the lesion, the balloon is attached to the distal end of a small diameter catheter, which includes means for inflating the balloon from the other end of the catheter. The catheter is maneuvered or "steered" through the patient's vessels to the site of the lesion with the balloon in an un-inflated form. When the un-inflated balloon is properly positioned at the lesion, the balloon is then inflated to dilate the restricted area.

While angioplasty has been relatively successful in treating coronary artery disease, restenosis of the treated site often occurs approximately 3 to 6 months following the procedure. It is believed that the primary factor in developing restenosis is the healing that takes place after the injury caused by the intervention of balloon dilation procedure. The restenosis has close analogy to scar formation following vascular surgery in that the histologic result has a similar morphology. The histologic response is called myointimal hyperplasia. The process of myointimal hyperplasia consists of the migration of smooth muscle cells through the internal elastic lamina into the vessel lumen where they then proliferate. The net result is a thickening of the vessel wall. Over time, this thickening re-occludes or re-stenoses the vessel to a point where it is clinically significant. That is, the blood flow through the vessel is diminished to a rate similar to the rate before the angioplasty procedure. The occurrence of this seems to happen approximately 30–35% of the time following an angioplasty to that specific site in coronary arteries.

Several alternative procedures have been attempted to try to affect the occurrence or rate of the restenosis following intervention to the lesion site in the coronary artery. These procedures have included the use of lasers, mechanical atherectomy devices, heated balloons, and metal implantable stents. While each of these procedures has shown some success in dealing with the initial lesion, all have the similar problem of restenosis at a similar or even greater occurrence. Current estimates of restenosis of the lesion site using these alternative procedures ranges between 40–50%. The time frame of restenosis of all of these is generally from 3–6 months after the procedure.

Therefore, it appears that this re-stenotic healing lesion area is independent of the type of interventional procedure used. Rather, it is a physiologic response to any type of injury brought to that lesion site. Because of this intervention independent physiologic response, it is felt by many physicians that potentially the best way to deal with restenosis would be by a pharmacologic means, such as a drug agent, targeted at the biochemical events that take place after injury.

To date, most pharmacologic trials involve either an oral or intravenously injected drug that is delivered throughout the whole body in hopes of trying to effect this small site in the arteries. This type of pharmacologic treatment is known as a "systemic treatment." Some agents that have been tried in human clinicals include: heparin, calcium channel blockers, angiotensin converting enzyme inhibitors, Omega-3 fatty acids, and growth peptides. Other agents that may not have been tried in clinicals but are of interest include thromboxane synthetase inhibitor, serotonin, growth factor inhibitors, growth factor analogs such as angiopeptin, antagonists, HMGCoA reductase inhibitors, platelet derived growth factor, inflammatory cell factors, platelet aggregation inhibitors, and thrombin inhibitors such as hirudin or its analogs.

The indication for use of most of these has been either in vitro-cell culture studies or animal studies. These studies have shown some effect on the smooth muscle cell proliferation and migration which are major components of the myointimal hyperplasia that takes place in the restenotic lesion. However, none of the systemic drug delivery human trials to date has shown a major effect on the occurrence of restenosis.

Even though none of these agents have been completely successful in the in-vivo human clinical trials, it is still generally felt that one of these agents or some other new agent, if delivered locally and site specifically to the lesion, would still be able to reduce the proliferative response. One of the problems with systemic techniques is the inability to deliver a high enough concentration of the agent locally at the lesion in order to effect the physiologic response. In the in-vitro and in-vivo animal studies which have shown some success, a high concentration of the agent was used. Thus, it is believed that if the agent was delivered specifically to the site as opposed to systemically, the agent may be delivered at a high enough concentration to truly effect the physiologic response.

The reason many of these agents have not been used in a higher concentration in-vivo in humans is that many of the agents may exhibit undesirable side effects. Thus, if a high concentration of the agents is given systemically, they may have unwanted physiologic effects. Therefore, if the drug can be given with high concentrations locally to the vessel wall while minimizing the systemic amount of drug, the desired result of modulating the restenotic growth while preventing any unwanted systemic effects may be achieved.

There are other ways known to date in trying to create a site specific local delivery of drug to a site. One approach presently contemplated is the use of a perforated or sweating balloon. For example, a drug delivery device is disclosed by Wolinsky, H., et al. in the article entitled, *Use of a Perforated Balloon Catheter to Deliver Concentrated Heparin Into the Wall of a Normal Canine Artery,* 15 JACC 475 (Feb. 1990). This device is a percutaneous transluminal coronary angioplasty (PTCA) balloon with several microholes in the balloon for delivery of an agent during balloon dilatation. The drug is incorporated into the same fluid which is used to inflate the balloon.

A disadvantage of available devices, such as the one disclosed by Wolinsky et al., is that these devices cause a substantial blockage of blood flow in the subject vessel during the procedure. Thus, such devices may only be used for the fairly short time frame (typically, from one to two minutes), similar to the time frame of the actual angioplasty dilatation.

Other available drug delivery devices are disclosed, for example, in U.S. Pat. No. 4,824,436 (Wolinsky) and U.S. Pat. No. 4,636,195 (Wolinsky). These devices are directed to a dual occlusion catheter in which a balloon is inflated proximally and distally of the accumulation or lesion creating a space for infusion of a drug. This dual balloon catheter creates a space for infusion of drug separate from the blood flow. This device, however, also can only be used for a short period of time because it occludes blood flow.

In these types of devices where a balloon is inflated inside the vessel, some means for providing perfusion through the catheter itself becomes important. It is necessary in such devices that the device provide a large latitude in time over which the agent could be delivered. Devices which occlude blood flow may not provide the necessary latitude. Because the basic research into the biochemistry and physiologic events indicate that the initial events begin immediately after injury and continue intensely for several hours, it is desirable for the drug delivery system to allow drug delivery for several hours to a day or two beginning immediately after intervention. This research also points out that the initial events subsequently create a cascade of events that ultimately lead to intimal thickening. While these accumulations or lesions do not become apparent for several months, it is felt that if these initial events can be modulated, blocked, or even accelerated, then the subsequent cascade can be altered and a diminished overall thickening could be achieved.

Some devices have been designed which permit localized delivery of a drug agent while providing enhanced perfusion capabilities. For example, the drug delivery catheter disclosed in co-pending U.S. patent application Ser. No. 07/740,045 filed on Aug. 2, 1991, commonly assigned to the Assignee of the present application, provides an inflatable perfusion lumen which provides significantly more perfusion area than previous drug delivery devices. The disclosed catheter and method also provides drug delivery pockets on the outer periphery of the perfusion lumen. The pockets allow the drug agent to be delivered site specifically for extended periods of time.

All of the drug delivery devices discussed above, however, require that the device remain in the vessel while the drug agent is being administered. It would be desirable to have a technique for delivering a drug agent locally without the need for the drug delivery device to remain in the vessel.

To this end, some techniques have been proposed wherein a drug is delivered by a surgical procedure where a drug agent is delivered to the outside of a vessel to be treated. Studies have shown that during administration by implanting a controlled release device which surrounds the vessel (periarterial drug administration) using drugs such as heparin-ethylenevinyl acetate significantly inhibited restenosis in an arterial injury model. See for example, Edelman et al., Proc. Natl. Acad. Sci. U.S.A., 87, 3773 (1990); and Edelman et al., J. Clin. Invest., 39, 65 (1992). In these types of procedures, access to the vessel is obtained by surgically cutting to the desired location in the vessel. Then the drug agent is maintained at the desired location by wrapping a band or cuff around the vessel with the agent being loaded into the band or cuff. Although periarterial drug administration has shown some initial success in an animal model, this procedure used for delivering the implant has the obvious disadvantage of being very invasive.

Therefore, it is desirable to have a drug delivery device capable of providing the necessary blood flow to the heart while the drug agent is being administered, which can be removed after the drug agent has been delivered and which is substantially less invasive than presently proposed techniques.

Such a device may also be extremely desirable in other procedures where a drug is to be delivered to a specific site in a vessel. For example, drug delivery devices may be useful in procedures where a drug or agent is used to dissolve the stenosis in an effort to avoid the use of angioplasty or atherectomy procedures altogether or to deliver a thrombolytic agent to dissolve a clot at the lesion site Such a device may also be useful in the treatment of various disorders involving other vessels or vessel-like lumens in the body.

It will be recognized from this discussion that there is a need for a generic type of drug delivery system which emphasizes physician control over the device and agent. The device should have flexibility as to the agent that is to be delivered and should be capable of delivering any number of agents (either separately or at the same time), or possibly also allow a change in the protocol of the delivery. It should also be flexible with respect to the time frame over which these agents would be delivered. It would also be desirable to have a device which can be removed from the vessel while the drug remains in place at the desired location.

Therefore, it is a primary object of the present invention to provide a device and method which can contain a relatively high concentration of a drug agent in a selected portion of a vessel, such as a blood vessel.

It is another object of the present invention to provide a device which can be removed after the agent has been delivered while the drug remains at the desired site.

It is a still further object of this invention to provide a device which is flexible as to the drug and the number of drugs or combination of therapeutic agents which can be delivered as well as the time frame over which they can be delivered.

SUMMARY OF THE INVENTION

To achieve these and other objects, the present invention provides a new and unique drug delivery catheter and method which may be inserted into a vessel, such as a blood vessel. The drug delivery technique of the present invention includes a catheter which comprises an elongated tubular shaft with an inner lumen and a vessel puncturing element which is housed in the lumen. The puncturing element has a retracted position such that it will not be in contact with the vessel wall as the catheter is guided through the vasculature. The inner wall that defines the lumen acts as a restraint that retains and holds the puncturing element in its retracted position. The puncturing element also has a puncturing position where it protrudes outwardly of the catheter shaft and engages and punctures the vessel wall. The puncturing element is configured such that it moves to the puncturing position when the restraint provided by the inner wall of the lumen is no longer being applied.

First, the catheter is inserted into the area to be treated. The puncturing element is then moved to its puncturing position and the inner surface of the vessel wall is punctured. A drug agent is then delivered through the puncture in the wall. The drug agent may be delivered either into the vessel wall itself or outside of the vessel wall. Thus, the drug will remain at a treatment site and diffuse, preferably in a time released manner to the treatment area. The drug will remain at the delivered site even after the drug delivery catheter has been removed from the vessel.

In a preferred embodiment, the puncturing element comprises a needle which also functions as a tube to deliver the drug.

In a preferred embodiment, the techniques of the present invention involves the implantation of a biodegradable material loaded with the drug agent in close proximity to the extravascular side of the vessel where the implant will remain and release the drug agent over a period of time.

The present invention provides a device and method for drug delivery in relatively high concentrations and which can be used in a relatively flexible time frame depending on the particular form of the drug being delivered.

Additional objects, advantages and novel features of the invention will be set forth in part in the description which follows and in part will become apparent to those skilled in the art upon examination of the following or may be learn by practice of the invention. The objects and advantages of the invention may be obtained by means of the combinations particularly pointed out in the appended claims.

BRIEF DESCRIPTION OF THE DRAWINGS

FIG. 1 shows side sectional view of an embodiment of the drug delivery catheter of the present invention.

FIG. 2 shows an enlarged sectional view of the embodiment of FIG. 1.

FIG. 3 shows an enlarged section view of the embodiment of FIG. 1 puncturing a vessel.

FIG. 7 shows a perspective view of a cam arrangement for the drug delivery catheter of the present invention taken along lines 7—7 of FIG. 8.

FIG. 8 shows a side sectional view of a cam arrangement for the drug delivery catheter of the present invention.

FIG. 9 shows a side view of another embodiment of the drug delivery catheter of the present invention with an inflatable balloon.

FIG. 10 shows a cross-section of the embodiment of FIG. 9 along line 10—10.

FIG. 15 shows another embodiment of a cam arrangement for the present invention.

FIG. 16 shows an embodiment of a manifold which can be used with the present invention.

DETAILED DESCRIPTION OF THE PREFERRED EMBODIMENTS

Referring now specifically to FIGS. 1–5, a preferred embodiment of the drug delivery catheter 20 of the present invention is illustrated. The drug deliver catheter comprises a tubular catheter shaft 21 which has a proximal end, connected to a manifold 32, and a distal end. The distal end of the catheter 20 is intended to be inserted into and placed at the treatment site in the vessel 23. The catheter shaft may be made of any suitable material such as a metallic tube (commonly known in the art as a hypotube), a polymer material, or polypropylene. An exemplary dimension for the shaft is a 4F (≈0.053") but for coronary applications a size of 8F or smaller will be suitable. An exemplary length for the catheter shaft 21 is 51" but for coronary applications lengths from 15" to 60" are suitable.

Figure 5:
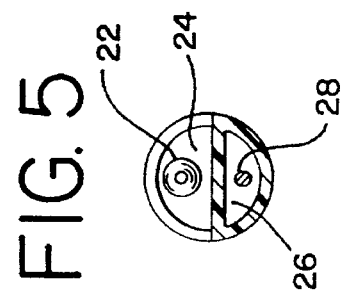
FIG. 5 shows a cross-section of the drug delivery catheter taken along line 5—5 of FIG. 6.
Figure 4:
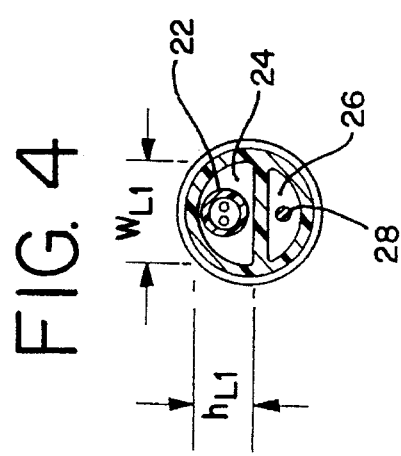
FIG. 4 shows a cross-section of drug delivery catheter taken along line 4—4 of FIG. 6.

Referring to FIG. 4, the catheter shaft 21 includes a first lumen 24 and a second lumen 26. The first lumen 24 is used to house and guide the vessel puncturing element of the drug delivery catheter 20. The second lumen 26 is used to house a guidewire or fixed wire 28 in order to advance the catheter to the desired location in a manner known in the art. In an exemplary embodiment, the first lumen 24 is "D" shaped and has a height $h_{L1}$ of about 0.022" and a width $W_{L1}$ of about 0.042" and the second lumen 26 has a height $h_{L2}$ of about 0.016" and a width $W_{L2}$ of about 0.023".

In the illustrated embodiment, the vessel puncturing device comprises a needle 22 which is bent at its distal end to define a short U-shaped portion. When the needle 22 is bent into this U-shape, it is in a retracted position. The bent needle 22 is positioned inside the first lumen 24 of the catheter shaft 21 such that the catheter 21 acts as a restraint holding the bent needle 22 in its retracted position. The bent tip 22a of the needle 22 defines the puncturing element. The needle defines a tube through which the drug agent may be delivered. Thus, with this preferred embodiment, the needle 22 functions as both the puncturing element as well as the drug delivery means. Preferably, the needle 22 is joined to a thicker tube 25 which may be bonded to another slightly larger tube. In an exemplary embodiment the needle 22 is a sharpened hypotube with an OD of 0.008" and an ID of 0.004". The needle 22 is bonded using cyanoacrylate to a polyamide tube 25 with an OD of 0.018" and an ID of 0.016" and a length of about 10". The tube 25 is in turn bonded using cyanoacrylate to a hypotube having an OD of 0.014" and an ID of 0.007" and a length of about 3.5'.

The needle 22 is comprised of a material which will provide a certain degree of opening force when the tip 22a is bent towards a position parallel with the catheter shaft 21. The amount of opening force will also depend on the angle φ of the bend and the length L of the tip 22a. In an exemplary embodiment, the needle 22 is a stainless steel hypotube with an angle φ in the completely opened or relaxed position being about 30° and the length L of the tip 22a being about 6 mm. Suitable materials for the needle or hypotube include spring steel, stainless steel, titanium, nitenol, a polymer or copolymer or some combination of these materials. The ID of the needle 22 may vary from less than 0.001" to about 0.131" and have OD from-smaller than 35 gauge to about 6 gauge. Exemplary OD's for the needle 22 for coronary applications are from 30 to 36 gauge.

Figure 6:
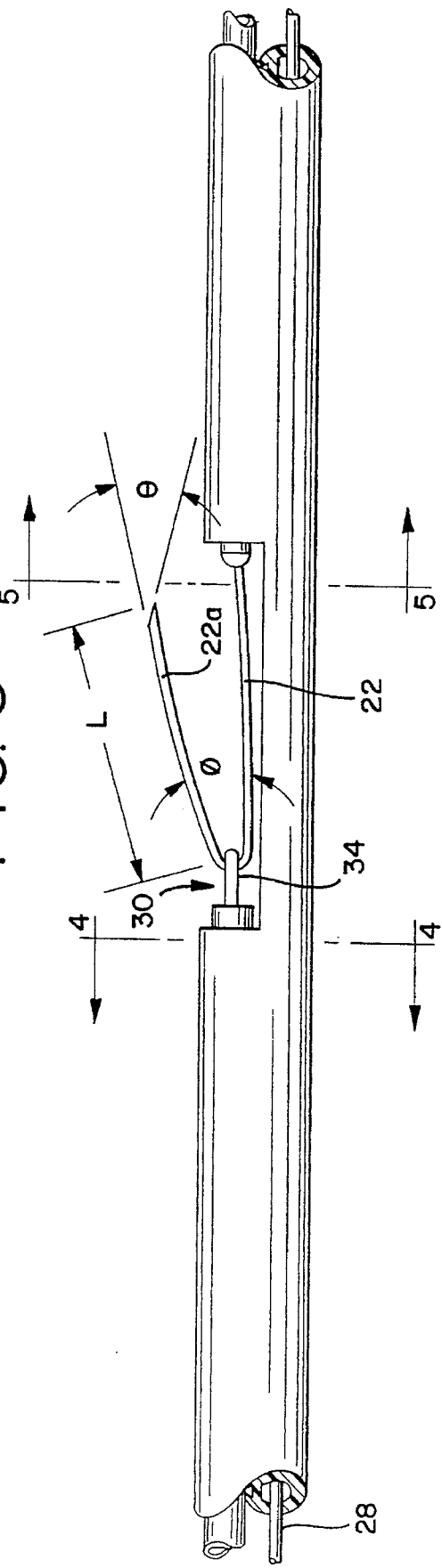
FIG. 6 shows an enlarged view of the puncturing area of the catheter of FIG. 1.

As illustrated in FIG. 6, the point of the tip 22a is preferably beveled at an angle θ for varied cutting effects. In an exemplary embodiment, the angle θ is about 25°. Patterns may also be formed on the sharpened end of the needle tip 22a to optimize its cutting or puncturing properties.

It will also be recognized that the lumen of the needle 22 may have various shapes. In an exemplary embodiment, the shape of the needle lumen is round, but the needle lumen may also be oval, rhomboid, trapezoidal, triangular, or rectangular.

Although only a single needle is illustrated in this embodiment, the drug delivery catheter 20 may comprise a multitude of needles.

Manifold 32 comprises an external body which has a port communicating with the guidewire lumen 26 for the introduction of the guidewire 28 through the catheter 20. The manifold 32 also includes an actuator which communicates with the needle 22 in such a way that a fluid can be delivered through the lumen in the needle 22. The actuator may comprise for example a syringe 33 which may be used to infuse the fluid into the needle 22. A suitable syringe is a standard luer lock 5 cc syringe available from Becton Dickinson. The infusion may also be accomplished by other methods such as an infusion pump or gravity.

Referring to FIG. 16, a manifold 32 includes the actuating element. The manifold 32 includes a manifold body 50 with grooves 51. A mating member 58 includes ribs 52 which slide into the grooves 51. The needle 22 (not shown in FIG. 16) is bonded to the end 54 of the member 58. A lock 56 formed of members 56a and 56b bonded together locks the body 50 to the engaging member 58 as the lock 56 is rotated. Thus, the needle 22 will move as the member 58 is moved and then is locked in the desired position.

As illustrated best in FIGS. 3 and 6, the catheter shaft 22 includes a window 30 near its distal end. When the distal tip 22a of the needle 22 is positioned such that it is distal of the distal portion of the window 30 (FIG. 2), the needle tip 22a is bent and housed completely within the catheter shaft 21 thus defining a retracted position for the puncturing element. As the needle 22 is pulled in a direction toward the proximal end of the catheter 20, the tip 22a of the needle 22 will begin to protrude radially outwardly and outside the perimeter of the catheter shaft 21 through the window 30. As the tip of the needle tip 22a protrudes outwardly, it will move until it engages the inner surface of the vessel wall 23. Upon further movement of the proximal end of the needle 22 in the proximal direction, the needle tip 22a will puncture the vessel wall 23 as illustrated in FIG. 3.

As illustrated in FIGS. 2, 3 and 6, the present invention may also include a trolley which is used to guide the needle 22 back into the window 30 when the needle 22 is advanced forward to move the needle 22 to its retracted position. In the illustrated embodiment, the trolley includes a wire loop 34 which surrounds the needle 22 and a plug 36 to which the wire loop 34 is attached. The plug 36 may be, for example, tubing filled with an adhesive. The wire loop 34 may be attached to the plug 36 by bonding or any other suitable method. The plug 36 and loop 34 can move freely in the axial direction in the inner lumen 24 of the catheter shaft 21. The plug 36 may also serve as a cam to inhibit rotation of the needle 22.

The location of the window 30 will be determined by the specific use contemplated for the device. In an exemplary embodiment used for coronary applications, the window 30 will be 3 mm long and disposed about 20 mm from the distal tip of the catheter 20. It will be recognized, of course, that the window size and location may vary for other applications such as peripheral applications.

As illustrated in FIGS. 7 and 8, the catheter 20 of the present invention may also include a plurality of cams 38 which act as anti-rotation means for the needle 22. The cams 38 may be bonded, to the hypotube and spaced at suitable distances apart. A suitable bond for the cams is cyanoacrylate. In the illustrated embodiment, the cams 38 are D-shaped and have a width of approximately 0.0418", a height of approximately 0.0223", a length of approximately 0.0844" and an inner aperture for the hypotube needle 22 having a diameter of approximately 0.019". These cams 38 may be made of a material such as platinum or PTFE or a combination of a polymer and metals. With such materials, the cams 38 may aid in the visualization of the movement of the needle tip 22a on a fluoroscope.

It will be recognized by those skilled in the art that other suitable anti-rotation means may be employed. For example, the needle 22 and lumen 24 may be provided with mating gears. FIG. 15 illustrates an embodiment where a gear 60 is bonded to the needle 22 and a mating gear 62 is formed in the tube 61.

It will also be possible to coat the inner diameter and outer diameter of the various tubes with materials such as teflon, silicone, or HPC to reduce friction between the sliding elements.

Figure 11:
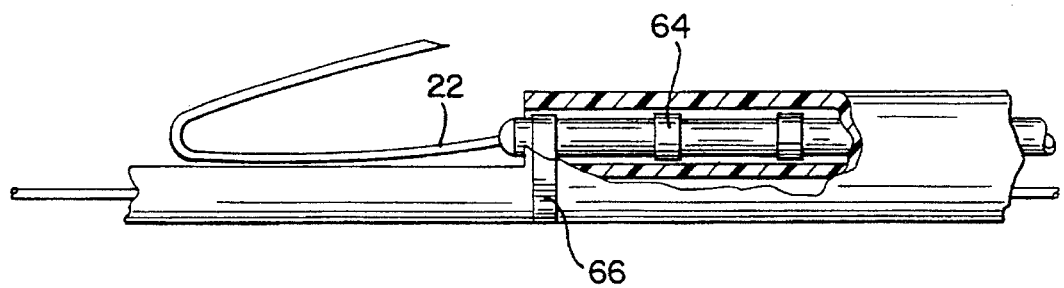
FIG. 11 shows an opening gauge for the catheter of the present invention.

Referring now to FIG. 11, the catheter of the present device may also include an opening gauge which is comprised of a plurality of markers 64 disposed on the hypotube 22 and a marker 66 on the catheter shaft 21. These markers may be made of a material such as platinum and bonded to the respective tubes. In this manner, the markers may be used to gauge the degree to which the tip 22a of the needle has opened and penetrated the vessel. It will be recognized that the plurality of markers may be disposed on the catheter shaft 21 and a single marker on the needle 22.

FIGS. 9 and 10 illustrate another preferred embodiment of the invention which includes an inflatable balloon 38. The balloon 38 is used to enable controlled placement/penetration of the needle 22. The balloon 38 is placed distally of the window 30 in the illustrated embodiment. It will be recognized, of course, that the balloon 38 may also be placed proximal of the window 30. This balloon 38 will stabilize or hold the shaft 21 at the desired position in the vessel as the needle 22 is retracted and opened to its puncturing position. The balloon 38 may also serve as a means for inducing hemostasis in the site of the puncture or it may be used for dilatation before, during, or after the delivery of the drug. It will be recognized that the balloon 38 may also be used to perform PTCA or similar procedures.

For the embodiment illustrated in FIGS. 9 and 10 which comprises the balloon 38, a third lumen is provided for inflating the balloon 38. FIG. 10 shows a cross-section of the catheter shaft which includes lumens 40, 42, and 44. These lumens 40, 42 and 44 may be used for a guide wire lumen, a lumen for the needle 22, and an inflation lumen for the balloon 38, respectively.

It is also possible that the device may be coated with a material which will make the needle 20 detectable or enhance its detectability by intravascular ultrasound. The location of the components of the delivery apparatus can then be determined with respect to one another via the use off a separate intravascular ultrasound probe, or a probe which is a component of the device itself. This will allow the physician to monitor the position of the needle as it enters its target site. It will also be recognized that the device may be coated with a material which will enable or enhance its visualization by methods such as MRI, CT scanning, X-Ray, Gamma camera imaging, or PET scanning.

The drug delivery catheter 20 of the present invention is used to deliver drugs to the desired treatment site as follows. The catheter 20 is guided to the site which is to be treated under fluoroscopy using standard PTCA guiding catheter and guidewire techniques. The catheter 20 is advanced such that the window 30 is placed at the particular site where the drug is to be delivered. The hypotube 22 is then pulled back such that the needle tip 22a exits radially outward from the window 30 and is inserted into the vessel wall 23. The needle tip 22a is then moved further radially outward until the tip 22a is at the desired location. The needle may be positioned to deliver the drug: between the inner and out surfaces of the vessel wall 23; to the adventitial side or outer surface of the vessel wall 23; or between the tissue 27 surrounding the vessel wall 23 and the outer surface of the vessel wall 23. The drug agent is then infused into the desired location using the syringe 33 attached to the manifold 32. Since the catheter does not block the flow of blood, the infusion may take place over almost any desired period of time. After the infusion is complete, the hypotube 22 is pushed forward to remove the needle tip 22a from the vessel wall 23 and to place the needle tip 22a into place within the distal tip of the catheter 20 parallel to the catheter shaft 21.

The illustrated embodiments uses a needle which is in a retrograde position. Since the needle is angled in this retrograde path, it is protected from being filled with flowing blood and causing dissection, and allowing the track to clot. It will, however, be recognized by those skilled in the art that other positions are possible. For example, the needle may protrude directly radially outward or may even project in a forward direction toward the distal end of the catheter 20.

Figure 12:
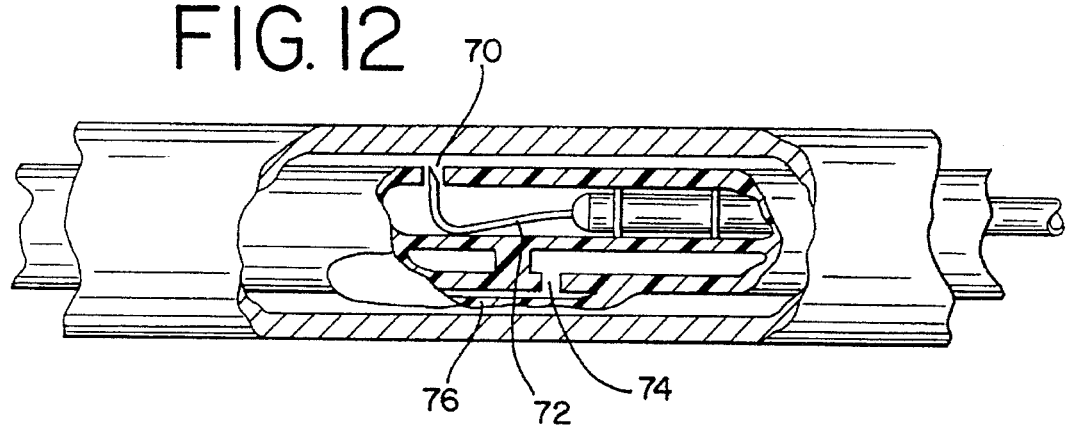
FIG. 12 shows another embodiment of the present invention with the puncturing element in the retracted position.
Figure 13:
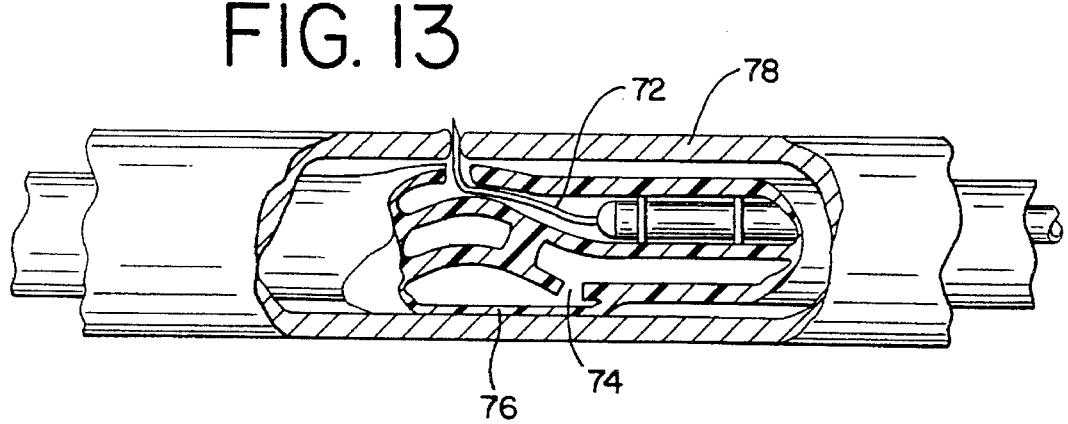
FIG. 13 shows the catheter of the embodiment shown in FIG. 12 with the puncturing element in the puncturing position.

FIGS. 12 and 13 show another embodiment of the drug delivery catheter of the present invention. In this embodiment, the needle 72 is moved to the puncturing position to puncture the wall of the vessel 78 (shown in FIG. 13) by means of an inflatable balloon 76. Inflation fluid is provided through an inflation port 74. When the window 70 has been positioned at the desired location, the balloon is inflated until the needle has puncture the wall.

Figure 14:
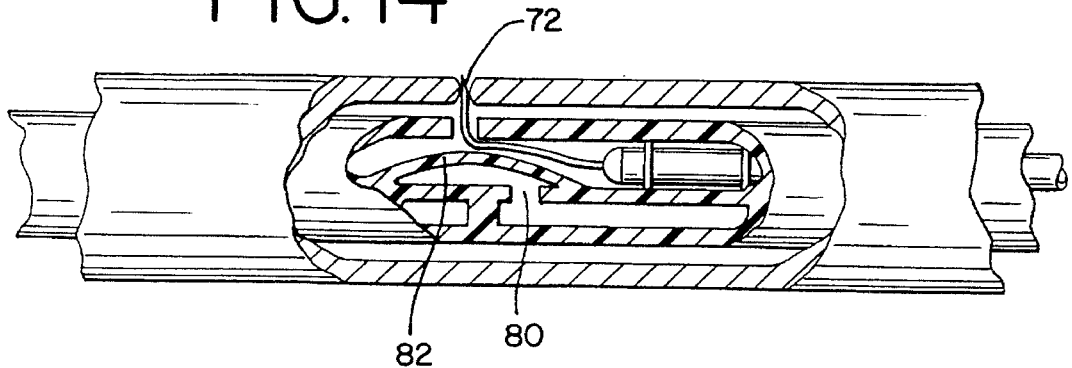
FIG. 14 shows another embodiment of the present invention with the puncturing element in the puncturing position.

FIG. 14 shows another embodiment where the needle 72 is moved by means of fluid pressure being applied to a flexible flap 82 through a port 80. The drug being administered itself may take various forms. For example, the drug may be delivered in the form of a polymeric rod or spike loaded with a drug which will be implanted next to the area which is to be treated. In this form, the rod or spike would be preloaded into the tip 22a of the needle 20 and would be ejected from the needle 20 as fluid pressure is applied by means of the syringe 38 to the other end of the needle 20. The catheter 20 may also be used to inject microcapsules loaded with the drug which will be placed in close proximity to the area to be treated. The catheter may also be used to deliver an emulsion of liposomes loaded with the drug which will be placed in close proximity of the area to be treated.

In these embodiments where the drug is encapsulated or loaded in a biodegradable material, the implants will remain and release the drug agent over a selected period of time after the catheter has been removed from the vessel. The device, however, can also be used to deliver the drugs in fluid for in high concentration between the outer wall of the vessel being treated and fatty tissue which surrounds the vessel. A list of potential drugs which may be used with the present invention is provided below in Table 1.

TABLE 1

| | |
|---|---|
| A Thrombolytic | A fragment of a glycoprotein |
| An Anti-thrombotic | A recombinant glycoprotein |
| An Anti-proliferative | A fragment of a recombinant glycoprotein |
| An Anti-platelet | A Carbohydrate or a fragment thereof |
| A Protein | An Antiarrhythmic |
| A Peptide | A beta blocker |
| A fragment of a recombinant peptide/protein | A calcium channel blocker |
| A fragment of a non-recombinant peptide/protein | A vasodilator |
| Genetic material | A vasoconstrictor |
| A recombinant peptide/protein | An inorganic ion or mixture thereof |
| A glycoprotein | |

Other steps may be used to further enhance the treatment provided by the present invention. For example, the needle can be heated or cooled to enhance the performance of the device. The catheter can be used to deliver and activate hot or cold activated drugs.

The needle can also be made to vibrate at various frequencies to enhance the performance of the device (i.e. to optimize drug delivery). For example, the catheter can be used to deliver and activate sonically activated drugs.

It is also conceivable that the device may have a conduction path for the conduction, transfer or passage of light such that the device will deliver a predetermined wave length of light to a specific portion of the vessel or body cavity, the vessel wall, or to a specific portion of the adventitia. The light may then be used to deliver and activate light-activated drugs. The catheter can be used to deliver a substance which will carry the energy of light through wave lengths and/or energy transitions or which will deliver a substance which will carry energy through wave lengths and/or energy transitions.

The device can also have selectively or non-selectively magnetized elements or can be used to induce an electric charge or induce a magnetic field in a selected area. The device can then be used to deliver and activate electrically-activated drugs.

Other uses for the catheter of the present invention are the delivery of a matrix to the exterior of a body lumen or cavity to structurally reinforce the area. A drug may be impregnated in this matrix and delivered coincidentally. The device may also be used to deliver a material that can be hardened in the wall or on the adventitial side. The hardened material may be used to form an extravascular stent or an intravascular stent depending on the precise delivery location.

The device may also be used to remove substances by using a vacuum in the needle lumen (microsuction).

Therefore, the device of the present invention provides a new and novel apparatus and technique which can be used to deliver drugs or other materials in close proximity to the extravascular side of a vessel. In addition to providing treatment for coronary disease, the present invention may be used to treat other disorders involving lumens or lumen-like vessels in the body such as prostatitis, the delivery of cancer chemotherapeutics, and the site specific delivery of controlled release antibiotics for the treatment of pericarditis, myocarditis, or endocarditis.

The present invention may also be used for delivering agents to the myocardium which have cardioprotective effects on myocardium exposed to a global or sub-global ischemic insult i.e. induced cardiologia during an "open heart" operation in which it is necessary to stop the heart and put the patient on cardiopulmonary bypass. Possible agents to be delivered include heat-shock proteins, hormones, ATP and its biochemical precursors, glucose or other metabolic carbohydrates. The treatment can allow the heart to recover function quicker after re-perfusion by reducing the "myocardial stunning" that occurs due to global ischemia.

The foregoing description of the preferred embodiments of the present invention has been presented for purposes of illustration and description. The disclosed embodiments are not intended to be exhaustive or to limit the invention to the precise forms disclosed, and obviously many modifications and variations are possible in light of the above teachings. It is intended that the scope of the invention be defined by the following claims, including all equivalent.

We claim:

1. A method of treating a vessel having a vessel wall with an inner surface, the method comprising the steps of:
   inserting a catheter having a vessel puncturing element disposed therein into a substantially tubular vessel;
   positioning the puncturing element at the site in the vessel to be treated;
   restraining said puncturing element such that it is maintained in a retracted position;
   placing said puncturing element in a puncturing position in which said puncturing element is no longer restrained;
   said puncturing element automatically moving in a direction substantially non-parallel with respect to a portion of said catheter that contains said puncturing element when said puncturing element is no longer being restrained.

2. The method of claim 1 further comprising the step of puncturing the vessel wall with the puncturing element at the site to be treated.

3. The method of claim 2 further comprising the step of delivering via a delivery means a drug outside of the inner surface of the vessel wall through the puncture in the vessel wall.

4. The method of claim 3 wherein the step of delivering the drug comprises delivering the drug into the vessel wall.

5. The method of claim 3 wherein the step of delivering the drug comprises delivering the drug to the outer surface of the vessel wall.

6. The method of claim 3 wherein the step of delivering the drug comprises delivery of the drug into tissue surrounding the vessel wall.

7. The method of claim 3 wherein the step of delivering the drug comprises the step of delivering a drug in a time release module.

8. The method of claim 3 wherein the delivery means includes said puncturing element having a drug delivery lumen and wherein the step of delivering the drug comprises delivering the drug through the drug delivery lumen.

9. The method of claim 1 wherein said drug comprises an antiproliferative drug for the treatment of restenosis.

10. The method of claim 1 wherein said drug comprises an antiproliferative drug for the treatment of vascular disease.

11. The method of claim 1 wherein said drug comprises a specific inhibitor of cellular proliferation.

12. The method of claim 1 wherein said drug comprises a specific inhibitor of thrombin.

13. The method of claim 1 wherein said drug comprises a specific inhibitor of platelets.

14. The method of claim 1 wherein said drug comprises a genetic material.

15. The method of claim 1 wherein said drug comprises a genetic material that when incorporated into cells results in the expression of therapeutic materials.

16. The method of claim 1 wherein said drug is incorporated into a time released matrix.

17. A method of treating a vessel having a vessel wall with an inner surface, the method comprising the steps of:
   inserting a catheter having a vessel puncturing element disposed therein into a substantially tubular vessel;
   positioning the puncturing element at the site in the vessel to be treated;
   inflating an inflatable compartment adjacent said puncturing element to thereby apply an adjacent force adjacent said puncturing element to move said puncturing element in a direction substantially non-parallel with respect to a portion of said catheter that contains said puncturing element, said adjacent force moving said puncturing element from a retracted position to a puncturing position.

18. The method of claim 17 further comprising the step of puncturing the vessel wall with the puncturing element.

19. The method of claim 18 further comprising the step of delivering via a delivery means a drug outside of the inner surface of the vessel wall through the puncture in the vessel wall.

20. The method of claim 19 wherein the step of delivering the drug comprises delivering the drug into the vessel wall.

21. The method of claim 19 wherein the step of applying said force moves said puncturing element a predetermined distance such that said drug is delivered to an outer surface of the vessel wall.

22. The method of claim 19 wherein the step of delivering the drug comprises delivery of the drug into tissue surrounding the vessel wall.

23. The method of claim 19 wherein the step of delivering the drug comprises the step of delivering a drug in a time release module.

24. The method of claim 19 wherein the delivery means includes said puncturing element having a drug delivery lumen and wherein the step of delivering the drug comprises delivering the drug through the drug delivery lumen.

25. The method of claim 17 wherein said compartment inflates a predetermined amount to move said puncturing element a predetermined distance.

26. A drug delivery device for treating a vessel having a vessel wall with an inner surface, the device comprising:
   an elongated catheter adapted to be inserted into the vessel;
   said catheter comprising a puncturing element having a retracted position in which said puncturing element does not puncture said vessel wall, at least a portion of said puncturing element being housed in a portion of said catheter when said puncturing element is in said retracted position;
   a restraint that contacts and holds said puncturing element in said retracted position;
   said puncturing element further having a puncturing position in which said puncturing element engages and punctures said vessel wall, said puncturing element being substantially non-parallel with respect to said portion of said catheter when said puncturing element is in said puncturing position;

said puncturing element automatically moving from said retracted position to said puncturing position when said restraint is no longer being applied; and delivery means coupled to said catheter and delivering a drug through a puncture in the vessel wall.

27. The device defined in claim 26 wherein:

said puncturing element further comprises a puncturing tip for puncturing said vessel wall when said puncturing element is in said puncturing position; and said catheter further comprises a window through which said puncturing tip extends when said puncturing element is in said puncturing position.

28. The device defined in claim 26 wherein said catheter further comprises:

an inflatable balloon coupled to said catheter; and an inflation lumen extending through said catheter for delivering inflation fluid to said balloon.

29. The device defined in claim 26 wherein:

said puncturing element further comprises an elongated shaft having a proximal and a distal end and an inner shaft lumen, and a needle, attached to said distal end of said shaft, having an inner needle lumen which is in fluid communication with said inner shaft lumen; and said delivery means comprises said inner shaft lumen and said inner needle lumen.

30. The device defined in claim 29 wherein said needle further comprises a puncturing tip for engaging and puncturing said vessel wall when said puncturing element is in said puncturing position.

31. The device defined in claim 30 wherein said puncturing tip includes an opening in communication with said inner needle lumen so that fluid in said inner needle lumen can flow out of said tip opening.

32. The device defined in claim 31 wherein said delivery means further comprises an injection device coupled to said inner shaft lumen for injecting fluid through said inner shaft lumen.

33. The device defined in claim 30 wherein said puncturing tip has a beveled edge for puncturing said vessel wall.

34. The device defined in claim 26 wherein said puncturing element comprises a needle having a tip for puncturing said vessel wall.

35. The device defined in claim 34 wherein:

said needle is bent into a substantially U-shape when said puncturing element is in said retracted position; and said needle is extended out to form a predetermined angle when said needle is in said puncturing position.

36. The device defined in claim 34 wherein:

said needle is bent to a first predetermined angle when said puncturing element is in said retracted position; and said needle is extended out to form a second predetermined angle when said needle is in said puncturing position.

37. The device defined in claim 34 wherein said needle is substantially parallel with said portion of said catheter when said needle is in said retracted position, said needle also being substantially non-parallel with said portion of said catheter when said needle is in said puncturing position.

38. A drug delivery device for treating a vessel having a vessel wall with an inner surface, the device comprising:

an elongated catheter adapted to be inserted into the vessel;

said catheter comprising a puncturing element having a retracted position in which said puncturing element does not puncture said vessel wall, at least a portion of said puncturing element being housed in a portion of said catheter when said puncturing element is in said retracted position;

said puncturing element further having a puncturing position in which said puncturing element engages and punctures said vessel wall, said puncturing element being substantially non-parallel with respect to said portion of said catheter when said puncturing element is in said puncturing position;

a movable surface comprising an inflatable compartment coupled to said catheter and adjacent said puncturing element to contact and move said puncturing element from said retracted position to said puncturing position when said movable surface is moved toward said puncturing element.

39. The device of claim 38 wherein said movable surface is moved toward said puncturing element by inflating said inflatable compartment.

40. The device of claim 38 further comprising delivery means coupled to said catheter for delivering a drug outside the inner surface of the vessel wall through a puncture in the vessel wall.

41. The device defined in claim 40 wherein:

said puncturing element further comprises a puncturing tip for puncturing said vessel wall when said puncturing element is in said puncturing position; and said catheter further comprises a window through which said puncturing tip extends when said puncturing element is in said puncturing position.

42. The device defined in claim 40 wherein:

said inflatable compartment comprises an inflatable balloon; and an inflation lumen extends through said catheter for delivering inflation fluid to said balloon.

43. The device defined in claim 40 wherein:

said puncturing element further comprises an elongated shaft having a proximal and a distal end and an inner shaft lumen, and a needle, attached to said distal end of said shaft, having an inner needle lumen which is in fluid communication with said inner shaft lumen; and said delivery means comprises said inner shaft lumen and said inner needle lumen.

44. The device defined in claim 43 wherein said needle further comprises a puncturing tip for engaging and puncturing said vessel wall when said puncturing element is in said puncturing position.

45. The device defined in claim 44 wherein said puncturing tip includes an opening in communication with said inner needle lumen so that fluid in said inner needle lumen can flow out of said tip opening.

46. The device defined in claim 45 wherein said delivery means further comprises an injection device coupled to said inner shaft lumen for injecting fluid through said inner shaft lumen.

47. The device defined in claim 46 wherein said puncturing tip has a beveled edge for puncturing said vessel wall.

48. The device of claim 40 wherein said drug comprises an antiproliferative drug for the treatment of restenosis.

49. The device of claim 40 wherein said drug comprises an antiproliferative drug for the treatment of vascular disease.

50. The device of claim 40 wherein said drug comprises a specific inhibitor of cellular proliferation.

51. The device of claim 40 wherein said drug comprises a specific inhibitor of thrombin.

52. The device of claim 40 wherein said drug comprises a specific inhibitor of platelets.

53. The device of claim 40 wherein said drug comprises a genetic material.

54. The device of claim 40 wherein said drug comprises a genetic material that when incorporated into cells results in the expression of therapeutic materials.

55. The device of claim 40 wherein said drug is incorporated into a time released matrix.

56. The device defined in claim 38 wherein said puncturing element comprises a needle having a tip for puncturing said vessel wall.

* * * * *